(12) United States Patent
Bateman et al.

(10) Patent No.: US 10,799,659 B2
(45) Date of Patent: Oct. 13, 2020

(54) TRACHEOSTOMY TUBE ASSEMBLIES AND INNER CANNULAE

(71) Applicant: SMITHS MEDICAL INTERNATIONAL LIMITED, Ashford (GB)

(72) Inventors: Timothy Bateman, Hythe (GB); Andrew Thomas Jeffrey, Hythe (GB); Christopher John Woosnman, Great Sutton (GB)

(73) Assignee: Smiths Medical International Limited, Kent (GB)

( * ) Notice: Subject to any disclaimer, the term of this patent is extended or adjusted under 35 U.S.C. 154(b) by 358 days.

(21) Appl. No.: 15/578,266

(22) PCT Filed: May 27, 2016

(86) PCT No.: PCT/GB2016/000107
§ 371 (c)(1),
(2) Date: Nov. 30, 2017

(87) PCT Pub. No.: WO2016/198817
PCT Pub. Date: Dec. 15, 2016

(65) Prior Publication Data
US 2018/0133423 A1 May 17, 2018

(30) Foreign Application Priority Data

Jun. 11, 2015 (GB) .................................. 1510231.2

(51) Int. Cl.
*A61M 16/04* (2006.01)
*A61M 16/08* (2006.01)

(52) U.S. Cl.
CPC .... *A61M 16/0427* (2014.02); *A61M 16/0465* (2013.01); *A61M 16/0497* (2013.01); *A61M 16/0816* (2013.01)

(58) Field of Classification Search
CPC .......... A61M 16/0427; A61M 16/0465; A61M 16/0497; A61M 16/04; A61M 16/0816
(Continued)

(56) References Cited

U.S. PATENT DOCUMENTS 4,304,228 A * 12/1981 Depel ............... A61M 16/0465
128/200.26
6,135,110 A * 10/2000 Roy .................. A61M 16/0465
128/207.14

(Continued)

OTHER PUBLICATIONS

PCT International Search Report and Written Opinion, PCT/GB2016/000107, EPO dated Aug. 5, 2016.

*Primary Examiner* — Joseph D. Boecker
(74) *Attorney, Agent, or Firm* — Louis Woo (57) ABSTRACT

A tracheostomy tube assembly includes an outer tube (1) and an inner cannula (2) inserted in the outer tube. Two lugs (36) and (37) project outwardly from the inner cannula. The outer tube has a connector (15) that is rotatable and has catch members (28) and (29) that can be rotated into alignment with the lugs (36) and (37) on the inner cannula so as to retain the inner cannula in the outer tube. The inner cannula is removed by twisting the connector (15) through 90° so that the catch members (28) (and 29) move out of alignment with the lugs (36) and (37) to enable the inner cannula to be pulled rearwardly out of the outer tube.

3 Claims, 6 Drawing Sheets

(58) Field of Classification Search
USPC .................................................. 128/207.14
See application file for complete search history.

(56) References Cited

U.S. PATENT DOCUMENTS

| | | | |
|---|---|---|---|
| 6,248,099 B1 * | 6/2001 | Bell | A61M 16/0465 |
| | | | 604/264 |
| 2010/0307488 A1 | 12/2010 | Poulsen et al. | |
| 2012/0006330 A1 | 1/2012 | Barbot | |
| 2013/0269704 A1 | 10/2013 | Thomas et al. | |

* cited by examiner

TRACHEOSTOMY TUBE ASSEMBLIES AND INNER CANNULAE

This invention relates to tracheostomy tube assemblies of the kind including an outer tracheostomy tube and an inner cannula removably inserted to extend along the bore of the outer tube.

Tracheostomy tube assemblies commonly include an outer tube and an inner tube or cannula that is a removable fit within the outer tube. The inner cannula can be removed and replaced periodically to ensure that the passage through the assembly does not become blocked by secretions. This avoids the need to remove the outer tube frequently.

The inner cannula presents various problems because it must be thin walled and a close fit within the outer tube so as to provide a large bore and thereby limit the resistance to flow of gas along the assembly. It must, however, also be sufficiently stiff to be inserted in the outer tube without buckling or kinking and must be readily removable, preferably with only minimal force being exerted on the tube. WO94/01156 and WO2004/101048 describe inner cannulae made of PTFE. EP1938857 describes an arrangement of tracheostomy tubes and inner cannulae where the hubs of the inner cannulae of different sizes are shaped differently so that they will only fit in the appropriate tracheostomy tube. EP2224985 describes an arrangement for attaching a hub to the shaft of an inner cannula. GB2056285 describes an inner cannula having a wall corrugated both externally and internally and a longitudinal groove or other reinforcement member traversing at least some of the corrugations. U.S. Pat. No. 4,817,598 describes a smooth-walled inner cannula having a ring-pull formation at its rear, machine end. U.S. Pat. No. 5,119,811 describes an inner cannula with a flared patient end and formed of two layers of different materials. U.S. Pat. No. 5,386,826 describes an inner cannula with an outer helical filament or layer of low friction material. U.S. Pat. No. 5,983,895 describes an inner cannula with straight sections at opposite ends joined by an intermediate curved section. U.S. Pat. No. 6,019,753 describes an inner cannula with two elongate regions of different flexibility so that the cannula has a plane of preferential bending. U.S. Pat. No. 6,019,753 describes an inner cannula having a shaft formed with slots to make it more flexible, the slots being covered by an outer thin sheath. U.S. Pat. No. 6,135,110 describes a curved inner cannula that is retained with the outer tube by means of a rotatable spring fitting. U.S. Pat. No. 4,304,228 describes a tracheostomy tube assembly with an inner cannula retained by a rotatable ring. Tracheostomy assemblies are also available where the inner cannula is attached with a 15 mm male tapered connector that is screw threaded onto the hub of the tracheostomy tube. These arrangements have the advantage that they reduce the pulling and pushing force otherwise needed to remove and insert an inner cannula. The problem with such arrangements, however, is that, when the inner cannula is removed the tracheostomy tube lacks a connector. There is also a risk that the connector may become unscrewed from the tube inadvertently when connected in a breathing circuit and cause leakage of ventilation gas, thereby preventing effective ventilation. Other inner cannula arrangements are described in, for example, U.S. Pat. No. 6,024,730, WO2014/132015, WO2014/132016, WO2015/110773, WO2015/118288, WO2015/136232, WO2015/145099, WO2015/166200, GB2531902 and PCT/GB2016/000069.

It is an object of the present invention to provide an alternative tracheostomy tube assembly and inner cannula.

According to one aspect of the present invention there is provided a tracheostomy tube assembly of the above-specified kind, characterised in that the inner cannula has a machine end fitting and a surface formation on its outer surface close to its machine end, that the outer tube has a male connector at its machine end adapted to mate with a cooperating female connector, that the machine end fitting on the inner cannula is received in the male connector, that the male connector rotatable member towards its machine end that is rotatable through at least a limited extent between a locking and unlocked position, that the male connector rotatable member has a surface formation on its inner surface adapted to engage the surface formation on the inner cannula in the locked position to prevent the inner cannula being withdrawn from the outer tube, and that the connector rotatable member is rotatable to the unlocked position where the surface formation on the connector is disengaged from the surface formation on the inner cannula such that the inner cannula can be slid out of or into the outer tube.

The surface formation on the inner cannula preferably includes a pair of projecting lugs. The inner cannula may have a surface formation located forwardly of its rear end and arranged to engage a rear end of the connector so as to provide a length of the inner cannula that can be gripped to enable the cannula to be pulled out of the connector.

According to another aspect of the present invention there is provided an inner cannula for use in a tracheostomy assembly according to the above one aspect of the present invention.

A tracheostomy assembly including an inner cannula, both in accordance with the present invention, will now be described, by way of example, with reference to the accompanying drawings, in which.

With reference first to FIGS. 1 to 5, the tracheostomy tube assembly comprises an outer tracheostomy tube 1 and a removable inner cannula 2 inserted within the outer tube. The outer tube 1 has a shaft 10 only the rear end of which is shown. The tube shaft 10 could be cuffed or uncuffed. At its rear or machine end 11 the outer tube 1 has a hub 12 and a laterally-extending flange 13 to which a retaining tape (not shown) can be fastened for securing the tube with the patient's neck. The outer tube 1 could have an internal diameter between about 2 mm and 10 mm, and its length could be between 60 mm and 200 mm. The hub 12 has a 15 mm male connector 15 in the form of a cylindrical plastics moulding secured with the hub (removed in FIG. 1 to expose the interior), the connector having a tapered outer surface 16, which is adapted to mate with the inside surface of a cooperating female connector (not shown). The connector 15 has an inwardly-facing annular lip 17 (FIG. 2) at its forward, patient end to the rear of which extends an annular recess 18. A short collar 19 projects rearwardly from the hub 12 within the forward end of the connector 15, the collar having an outwardly-projecting lip 20 with an inclined face 21. The lip 20 on the hub 12 is aligned with the recess 18 around the connector 15 and is snapped into the recess to form a permanent attachment of the connector to the hub. The attachment provided in this way enables the connector 15 to be rotated relative to the hub 12 about the axis of the hub and through only a limited angle of about one quarter of a turn, that is, 90°.

Figure 1:
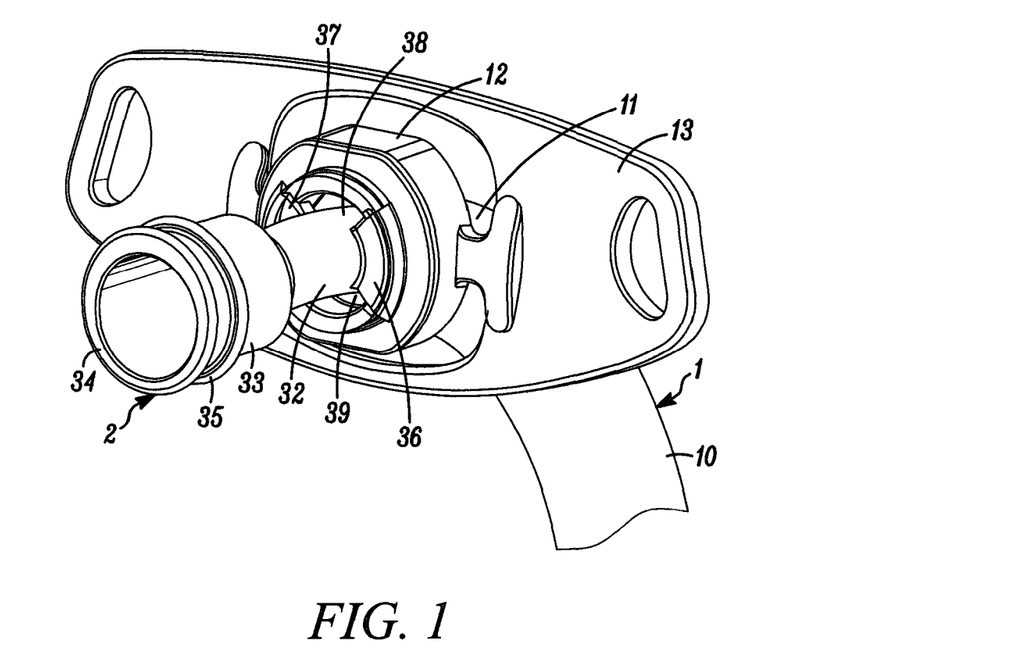
FIG. 1 is a perspective view of the machine end of the assembly with the connector of the outer tube removed.
Figure 2:
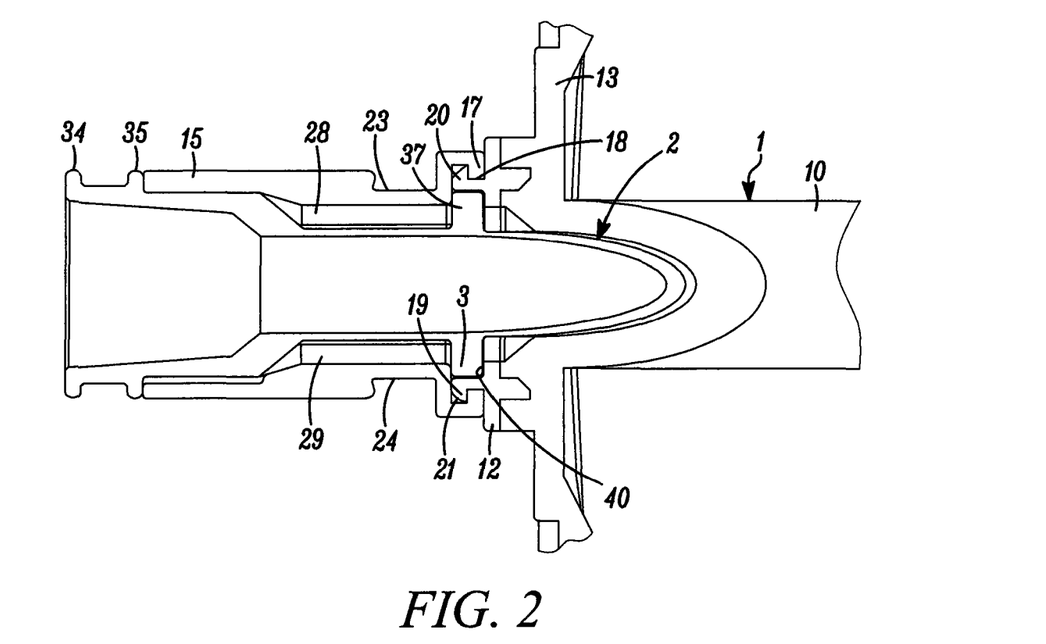
FIG. 2 is a cross-sectional plan view of the machine end of the assembly with the inner cannula locked in position.
Figure 3:
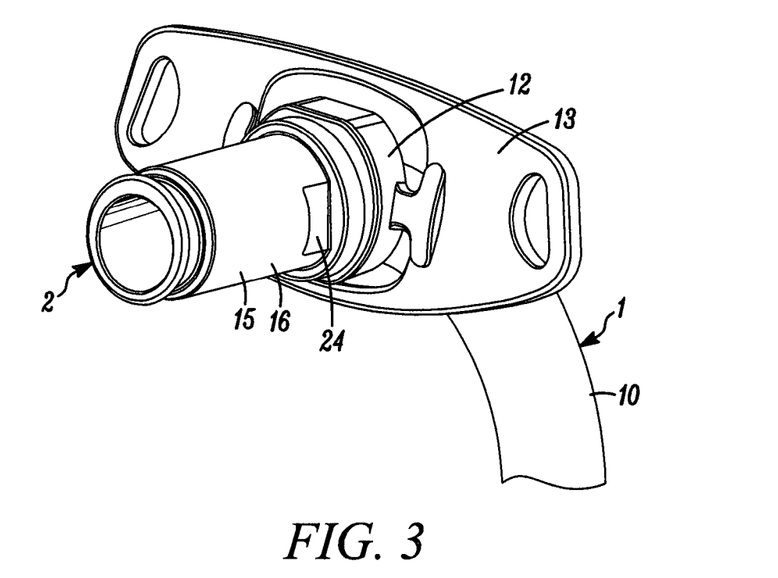
FIG. 3 is a perspective view of the assembly with the inner cannula locked in position.
Figure 4:
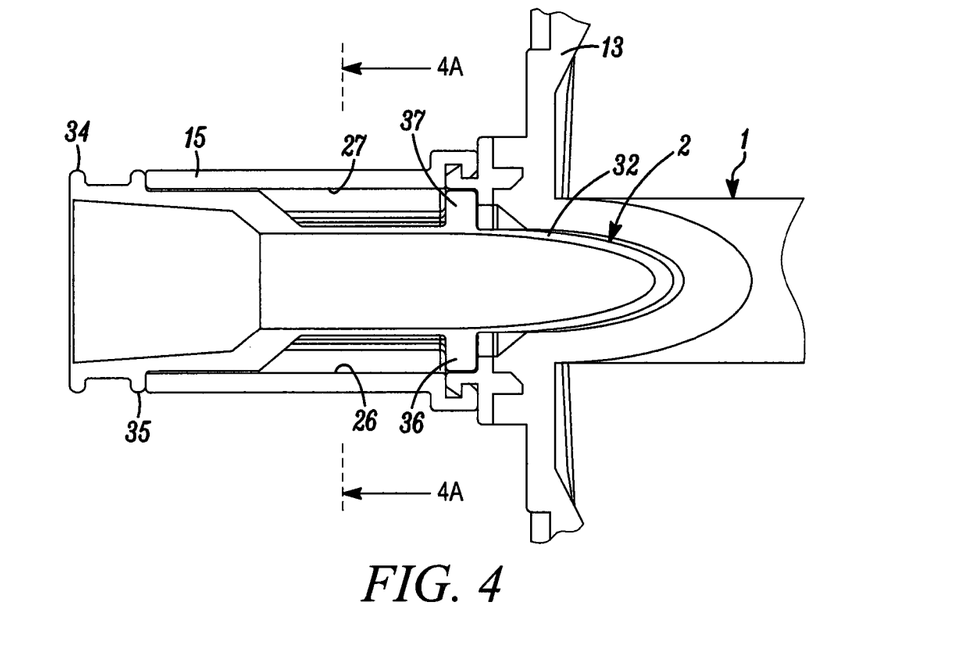
FIG. 4 is a cross-sectional side elevation view of the machine end of the assembly with the inner cannula unlocked.
Figure 4A:
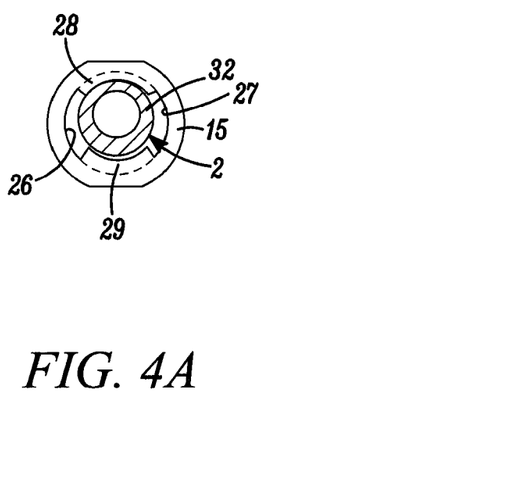
FIG. 4A is a transverse cross-sectional view of the assembly along the line 4A-4A of FIG. 4.

On its outer surface, the connector 15 has two alignment flats 23 and 24 extending parallel to one another close to the patient end of the connector. On its inner surface, the connector 15 has two parallel slots or keyways 26 and 27 extending along about half the length of the connector at its patient end (FIGS. 4 and 4A), the internal diameter of the connector across the slots being greater than the diameter between the slots. The two regions between the slots 26 and 27 provide catch members 28 and 29 respectively (FIGS. 2 and 4A).

Figure 5:
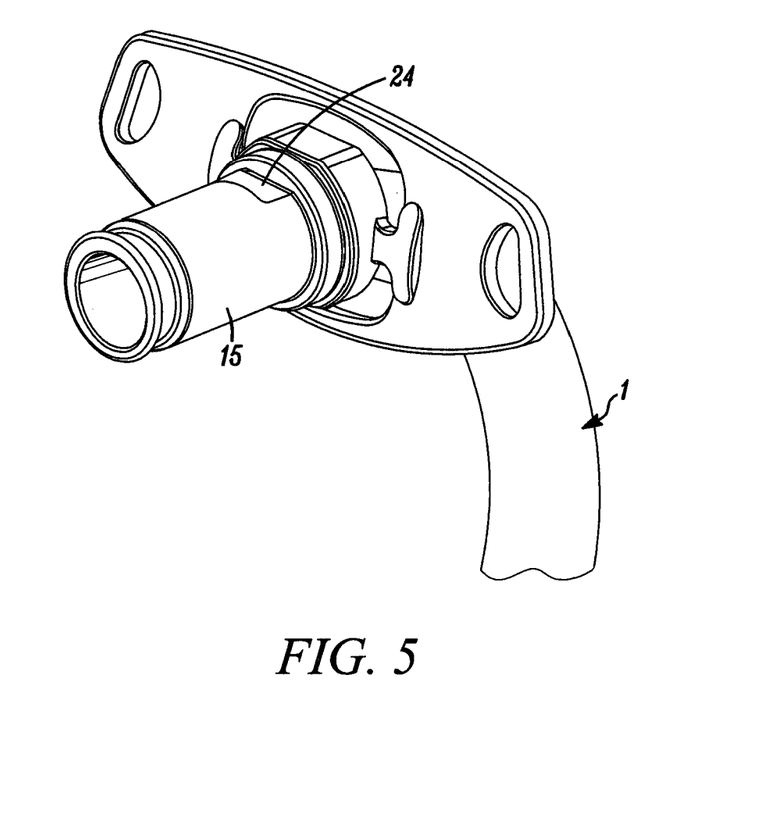
FIG. 5 is a perspective view of the assembly with the inner cannula unlocked.
Figure 6:
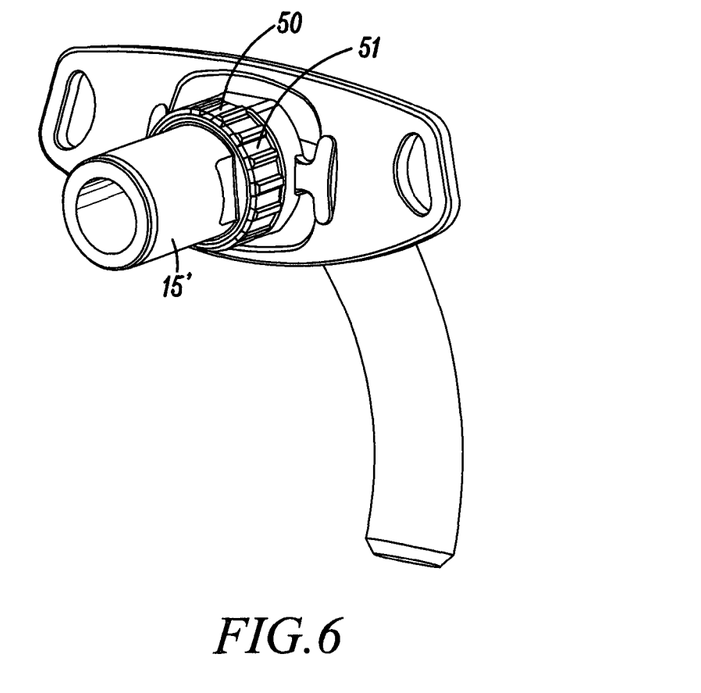
FIG. 6 is a perspective view of an alternative embodiment of the invention.

The inner cannula 2 includes a shaft 32 of circular section and of a thin, stiff plastics material, such as PVC, polyurethane, polyethylene, polypropylene, PTFE or other flexible or semi-rigid plastics material. The external diameter of the shaft 32 is selected, along most of its length, to be just smaller than the inner diameter of the shaft 10 of the outer tube 1 so that the inner cannula 2 can be readily inserted and removed from the outer tube. The shaft 32 is curved to the same curvature as the shaft 10 of the outer tube 1 in which it is to be used. The rear or machine end of the cannula 2 has an integral hub or machine end fitting 33 with a thicker wall than the shaft 32. The hub or machine end fitting 33 is shaped to locate and secure within the connector 15. More particularly, the hub 33 has a first radially enlarged rim 34 at its rear, machine end and a second enlarged rim 35 of the same diameter spaced forwardly of the first rim by about 5 mm. The second, forward rim 35 abuts the rear end of the connector 15 when the inner cannula 2 is fully inserted so that a short length of the cannula projects rearwardly to enable the cannula to be gripped and removed from the outer tube when necessary. The inner cannula 2 also has two wedge or segment-shape lugs or lock formations 36 and 37 that each extend around about 90° of the cannula on opposite sides. The lugs 36 and 37 project outwardly of the inner cannula 2 in opposite directions and extend at right angles to the plane of curvature of the inner cannula and the outer tube 1. The two lugs 36 and 37 are spaced from one another around the inner cannula by segment-shape gaps 38 and 39. The lugs 36 and 37 are positioned along the length of the shaft 32 of the inner cannula 2 so that the forward, patient-side face of the two lugs abut a rearwardly-facing annular surface 40 on the hub 12 when the inner cannula 2 is fully inserted in the outer tube 1. The dimensions of the two lugs 36 and 37 on the inner cannula 2 are such that they can be slid freely along the two slots 26 and 27 respectively in the connector 15 when this is appropriately oriented. More particularly, when the connector 15 is twisted fully anticlockwise, as shown in FIGS. 4 and 5, it is placed in an unlocked position where the two internal slots 26 and 27 are located on a line extending at right angles to the plane of curvature of the outer tube 1, that is, generally parallel to the length of the flange 13. With the connector 15 in this orientation the slots 26 and 27 align with the lugs 36 and 37 on the inner cannula 2 so that the cannula can be slid out of or into the outer tube 1.

To insert a new inner cannula 2 in the outer tube 1 the connector 15 is first twisted fully anticlockwise to its unlocked position. The inner cannula 2 is then pushed into the outer tube 1 to its full extent until the forward rim 35 on the inner cannula hub 33 abuts the rear end of the connector 15 in which position the forward, patient end of the inner cannula lies level with the patient end of the outer tube 1. The connector 15 is then twisted to its full extent clockwise through 90° to its locked position in which the forward end of the two catch members 28 and 29 on the inside of the connector align with the lugs 36 and 37 and thereby prevent the inner cannula 2 being removed from the outer tube 1. When it is necessary to remove the inner cannula 2, the connector 15 is simply twisted back anticlockwise to its unlocked position so that the catch members 28 and 29 move out of alignment with the lugs 36 and 37, which are instead aligned with the slots 26 and 27 along the connector, allowing the inner cannula to be withdrawn unimpeded.

Instead of locking the inner cannula in the outer tube by means of a surface formation on a rotatable member provided by the connector it would be possible to use a rotatable member separate from the connector to hold the inner cannula in place.

Figure 10:
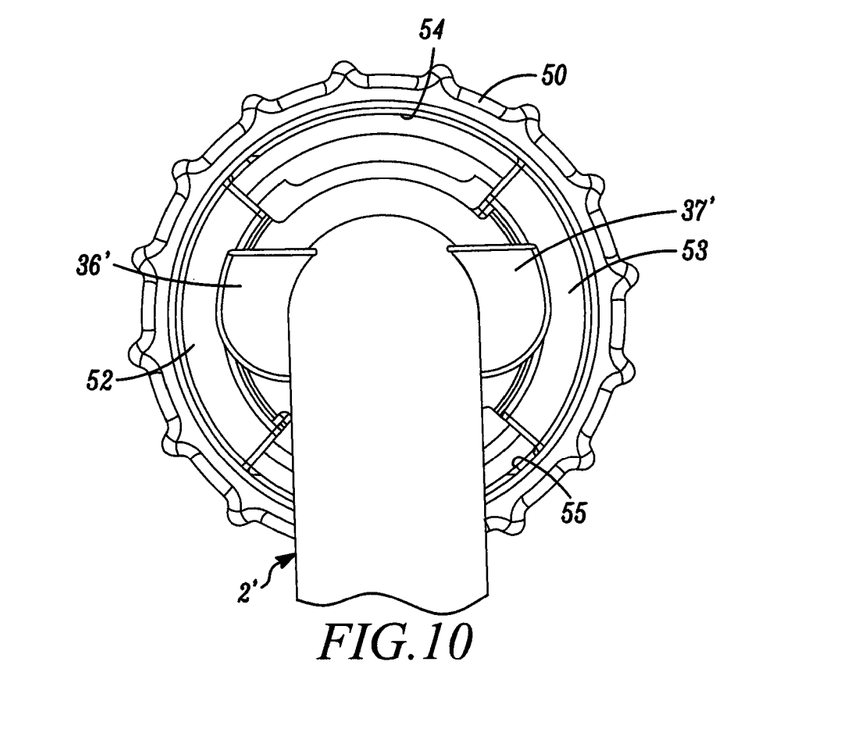
FIG. 10 is an end view of the alternative embodiment with the connector removed.

With reference now to FIGS. 6 to 10 there is shown an alternative embodiment with a fixed connector 15' that cannot be rotated and a rotatable locking ring 50 mounted on the hub 12' just forwardly of the connector. The locking ring 50 is circular with an outer knurled edge 51 to improve grip on the ring. The ring 50 has two wedge-shape catch members 52 and 53 (FIG. 9) projecting inwardly diametrically opposite one another, each extending around about 90°. The catch members 52 and 53 are separated from one another around the ring 50 by two wedge-shape slots or keyways 54 and 55 (FIG. 10).

Figure 7:
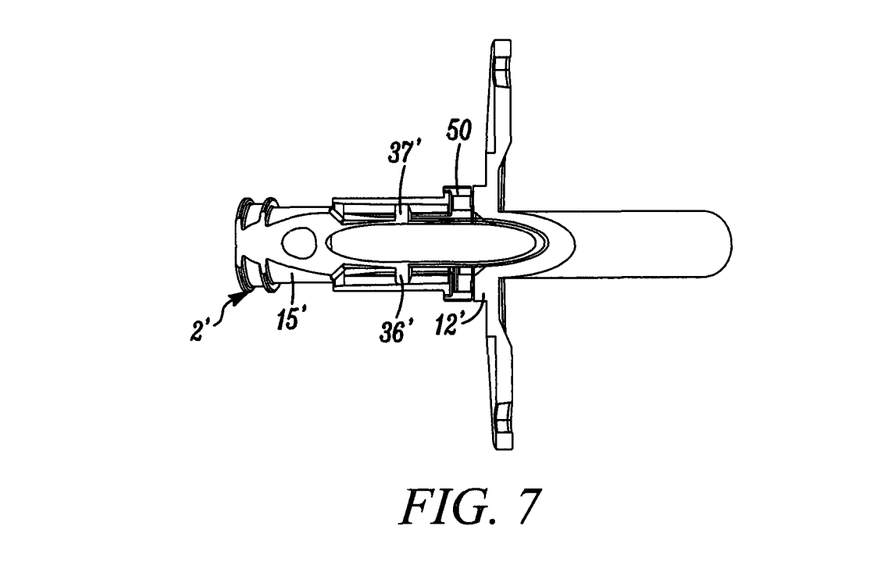
FIG. 7 is a cross-sectional plan view of the alternative embodiment with the inner cannula only partially inserted.
Figure 8:
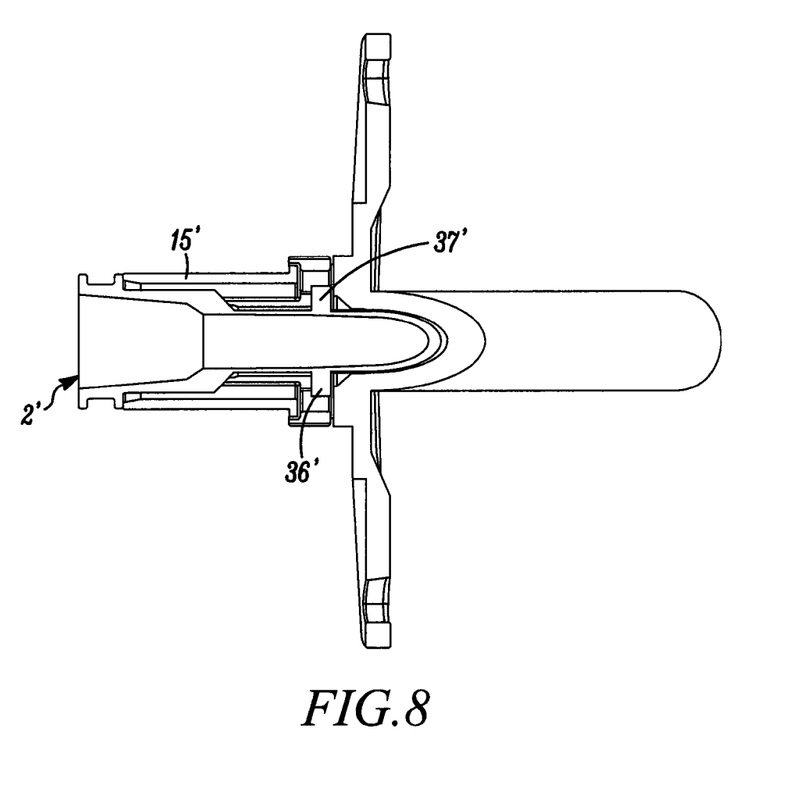
FIG. 8 is a cross-sectional plan view of the alternative embodiment with the inner cannula unlocked in the outer tube.
Figure 9:
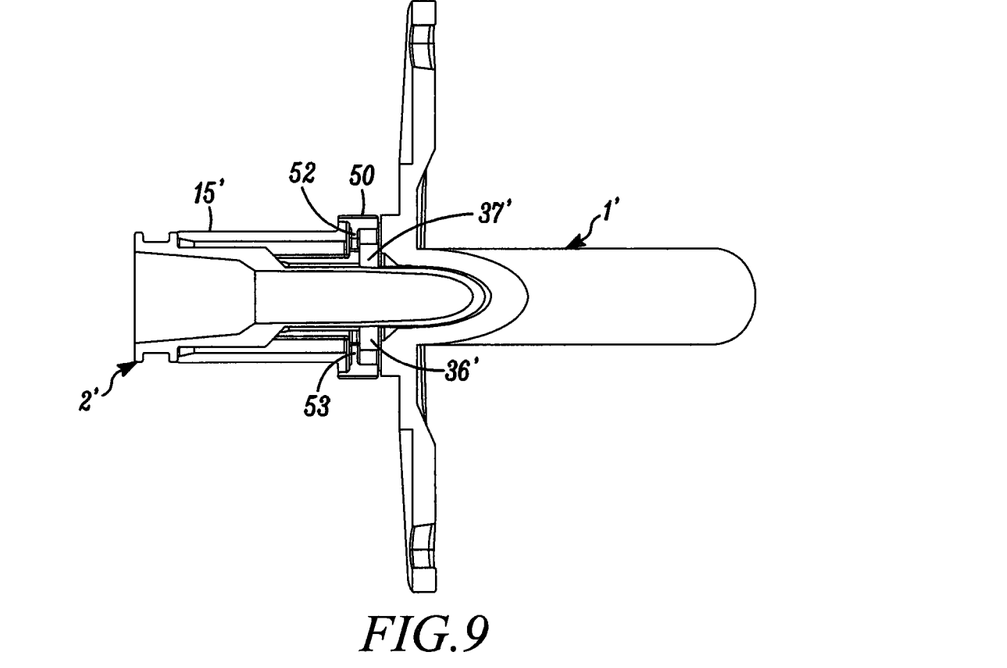
FIG. 9 is a cross-sectional plan view of the alternative embodiment with the inner cannula locked in position in the outer tube.

The inner cannula 2' in this assembly may be identical to the cannula 2 described with reference to the first embodiment, having two outwardly-projecting lugs or key formations 36' and 37'. When the rotatable locking ring 50 is rotated fully anticlockwise through 90° to its unlocked position, as shown in FIGS. 7 and 8 the inner cannula 2' can be slid freely into and out of the outer tube 1', the lugs 36' and 37' on the inner cannula being aligned with the slots 54 and 55 on the locking ring. With the inner cannula 2' fully inserted in the outer tube 1' the locking ring 50 is twisted fully clockwise through 90° so that the catch members 52 and 53 move around and to the rear of the lugs 36' and 37' to the position shown in FIGS. 9 and 10, thereby preventing the inner cannula being removed from the outer tube until the locking ring is returned to its unlocked position.

The present invention can be used to overcome a problem with those previous assemblies that rely on friction between the inner cannula and outer tube to hold the cannula in place because this means that relatively large forces have to be applied to the cannula to insert and remove it, thereby applying relatively large forces to the patient tissue around the stoma. The present invention also avoids the need to remove the connector to replace an inner cannula so that connection can be made to the tube whether or not the inner cannula is in place.

The invention claimed is:

1. A tracheostomy tube assembly including an outer tracheostomy tube and an inner cannula removably inserted to extend along a bore of the outer tube, characterised in that a machine end of the inner cannula has a machine end fitting and a locking formation on its outer surface, that the outer tube has a male connector at its machine end having a tapered outer surface adapted to mate with an inside surface of a cooperating female connector, that the machine end fitting on the inner cannula is received in the male connector, that the male connector is rotatable through at least a limited extent between a locked position and an unlocked position, that the male connector has a locking formation adapted to engage the locking formation on the inner cannula in the locked position to prevent the inner cannula being withdrawn from the outer tube, and that the male connector is rotatable relative to the inner cannula to the unlocked position where the locking formation on the male connector is disengaged from the locking formation on the inner cannula such that the inner cannula can be slid out of or into the outer tube.

2. An assembly according to claim 1, characterised in that the locking formation on the inner cannula includes a pair of projecting lugs.

3. An assembly according to claim 1, characterised in that the machine end fitting of the inner cannula has a surface formation located forwardly of its rear end and arranged to engage a rear end of the male connector so as to provide a length of the inner cannula that can be gripped to enable the cannula to be pulled out of the male connector.

* * * * *